(12) United States Patent
Leveugle et al.

(10) Patent No.: US 7,578,200 B2
(45) Date of Patent: Aug. 25, 2009

(54) METHOD AND APPARATUS FOR MEASURING PAPER SAMPLE STIFFNESS

(75) Inventors: Denys Leveugle, Kaysersberg (FR); Patrick Legrand, Saint Cloud (FR)

(73) Assignee: Georgia-Pacific France (FR)

( * ) Notice: Subject to any disclaimer, the term of this patent is extended or adjusted under 35 U.S.C. 154(b) by 250 days.

(21) Appl. No.: 11/755,129

(22) Filed: May 30, 2007
(Under 37 CFR 1.47)

(65) Prior Publication Data
US 2008/0053231 A1    Mar. 6, 2008

(30) Foreign Application Priority Data
May 31, 2006    (FR)    .................................. 06 51993

(51) Int. Cl.
*G01N 33/34* (2006.01)
*G01N 29/40* (2006.01)
*G01N 29/42* (2006.01)
*G01N 29/46* (2006.01)
*G01N 3/08* (2006.01)

(52) U.S. Cl. .............................. 73/801; 73/835; 73/159; 73/866

(58) Field of Classification Search .................. 73/159, 73/866, 801, 835
See application file for complete search history.

(56) References Cited

U.S. PATENT DOCUMENTS

| | | | | |
|---|---|---|---|---|
| 3,060,719 | A | * | 10/1962 | Pearlman .......................... 73/7 |
| 3,126,579 | A | * | 3/1964 | Janszen ....................... 28/241 |
| 3,683,681 | A | | 8/1972 | Taylor |
| 4,463,607 | A | | 8/1984 | Hilton |
| 4,596,152 | A | | 6/1986 | Lehtikoski et al. |
| 4,622,853 | A | * | 11/1986 | Leugers ...................... 73/597 |
| 4,869,101 | A | | 9/1989 | Dvorsky |
| 5,014,547 | A | * | 5/1991 | Holroyd ...................... 73/105 |
| 5,808,199 | A | * | 9/1998 | Kazys et al. .................. 73/597 |
| 5,974,883 | A | * | 11/1999 | Ross ........................... 73/587 |
| 6,026,681 | A | * | 2/2000 | Wunderer et al. ............. 73/159 |
| 6,486,962 | B1 | * | 11/2002 | Telschow et al. ............ 356/503 |
| 2003/0150270 | A1 | | 8/2003 | Bueno-Bigue et al. |

FOREIGN PATENT DOCUMENTS

DE    19712650 A1 *   10/1998
FR    2810111 A1      12/2001

* cited by examiner

*Primary Examiner*—Hezron Williams
*Assistant Examiner*—Rose M Miller
(74) *Attorney, Agent, or Firm*—Joel T. Charlton

(57) ABSTRACT

A method for measuring the rigidity of paper or other products made from cellulose fibers wherein the paper is torn and a digitized sound recording is made during the tearing process which is then analyzed to determine the percentage of time during which characteristic frequencies are present during the tearing process. It has been found that this percentage correlates well with rigidity.

12 Claims, 3 Drawing Sheets

METHOD AND APPARATUS FOR MEASURING PAPER SAMPLE STIFFNESS

This application claims priority to copending French patent application number 06 51993, filed May 31, 2006, the disclosure of which is incorporated herein by reference.

The present invention relates to the field of cellulosic fibrous products, especially paper and more particularly the papers that are normally referred to by the expression toilet and domestic papers. Its object is a method and a device for measuring the stiffness of these products.

The perception of the softness of a sample of this type of product that is held in the hand depends on several parameters including stiffness, or its opposite, suppleness, and resilience.

Furthermore, in certain cases there are attempts to estimate the effect of a treatment on the stiffness of the end product. Thus, for example, it would be desirable to be able to monitor in a simple manner the evolution of the stiffness of a paper as a function of the refining of the pulp.

A proposal has already been made to analyse the sound that the paper emits when it is handled, crumpled, rubbed in order to characterize some of its properties.

Therefore, document U.S. Pat. No. 3,683,681 describes a device arranged to continuously crumple a strip of paper and therefrom give a measure of a characteristic via an audible sound signal which depends on the ultrasounds emitted by the crumpling.

Document U.S. Pat. No. 4,869,101 describes a device designed to crumple, also continuously, a strip of paper against a piezoelectric film whose resultant signals may be subjected to a frequency spectrum analyser. The spectrum obtained may then characterize the product. Another version of this approach is divulged in document FR 2 810 111.

However, these documents do not truly provide a method of quantitative characterization and restrict themselves to describing means of evaluation.

The applicant has therefore sought a method of quantitative measurement that is both effective and objective.

The method according to the invention of measuring the stiffness (D) of a paper or other cellulosic fibrous product is characterized in that a sample of the paper is torn, the sound generated during the tearing is recorded and the recorded sound is analysed so as to measure a percentage (pc) of the presence of frequencies characteristic of the tearing, this percentage being an indicator of the stiffness of the paper.

The invention therefore provides the paper manufacturer with a simple method using means that are easily available.

More precisely, the method is characterized in that it comprises the following steps:
the paper is torn in a first step with a predetermined force;
a recording is made during this step and a digitization is performed on the recorded sounds at a predetermined sampling frequency and with a predetermined resolution to obtain a digital recording of a predetermined duration;
in a second step, the digital recording is analysed in the temporal and frequency domains and a percentage of the presence of the frequencies characteristic of the tearing is measured over the said predetermined duration in order to deduce a stiffness index therefrom.

Preferably, the paper is torn in the line of its direction of travel.

Through this method with rigorously pre-established rules, it has been possible to establish at least one linear computational relation of the stiffness index as a function of the percentage of the presence of the said characteristic frequencies in the set of frequency spectra obtained over the duration of the recording.

Preferably for this:
a Fourier transform (FFT) is carried out based on the digital recording to obtain the said set of spectra encoded in amplitudes according to a colour scale so as to differentiate the frequencies of amplitudes at least equal to a predetermined minimal amplitude and sufficiently to be able to make the selection thereof.
the said set of spectra is limited to a zone, called test zone, comprising only the frequencies greater than a predetermined minimal frequency and, in this test zone, the relative surface area occupied by the frequencies of amplitudes at least equal to the said minimal amplitude is computed.
the stiffness index is computed based on the said relative surface area.

Advantageously, the test zone comprising a predetermined total number of pixels, the measurement of the relative surface area determining the stiffness index, is the number of colour pixels present on the said surface area, that can be easily evaluated thanks to a histogram function.

The invention also relates to a device for measuring the stiffness of a sample of paper for the application of the above method, characterized in that it comprises an apparatus, such as a tear tester, arranged to tear a sample of product in a manner that can be reproduced in identical conditions, a microphone and, connected to the microphone, computing means fitted with a sound card and sound recording and signal processing modules.

It is noted that, by this method and thanks to the system applying it, an objective measurement of the stiffness of the paper is obtained perfectly repetitively.

Other features and advantages of the present invention will more clearly appear on reading the following description, made with reference to the appended drawing in which.

Figure 1:
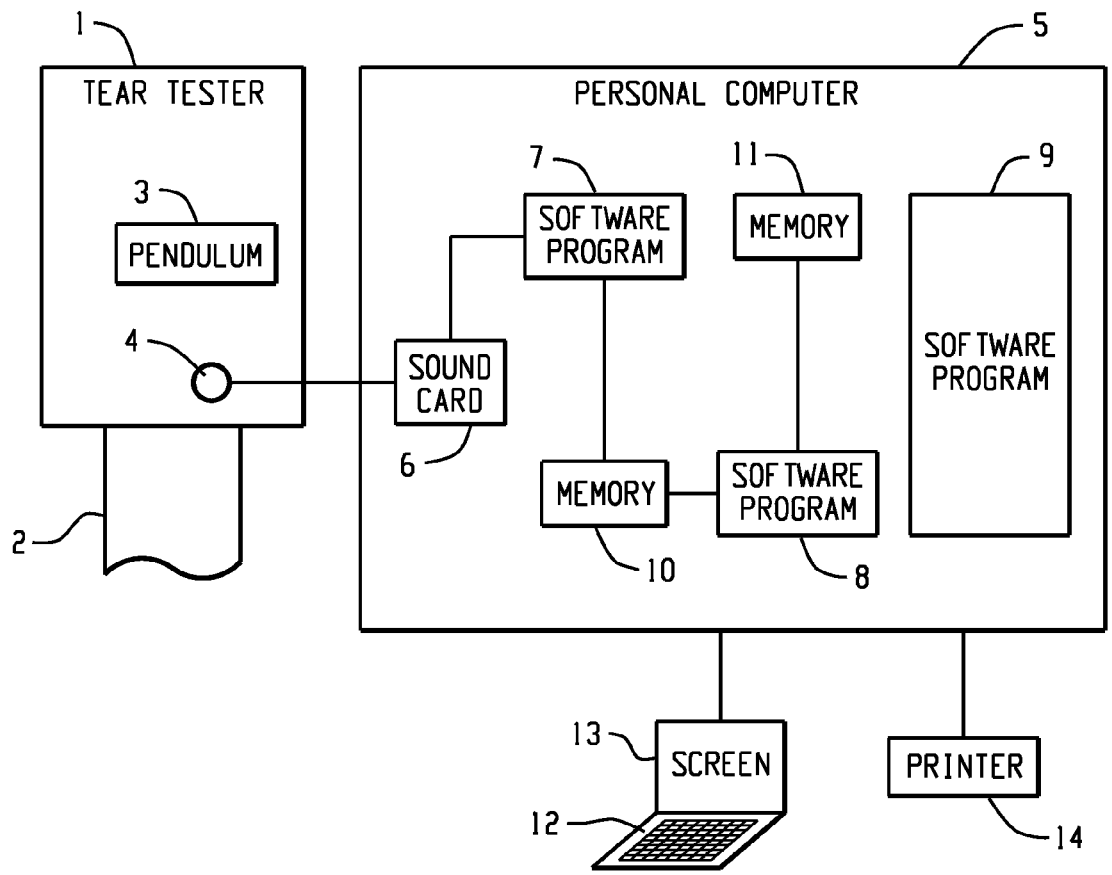
FIG. 1 is a functional block diagram of the system allowing the application of the method of measuring stiffness according to the invention.

The method proposed here for measuring the stiffness of a sample of paper consists, with reference to FIG. 1, in using a system of measurement comprising a tear tester 1 fitted with a microphone 4 connected to computing means, for example a personal computer or PC 5. The tear tester is an apparatus known per se that is used for example for measuring tear resistance values. Here it is diverted from its usual use.

The tear tester 1 is for example of the Adamel-Lhomargy brand, model ED20.

For the type of paper to be measured, for example toilet paper 10 by 12 centimeters in size, the pendulum 3 of the tear tester is loaded with a predetermined weight P equal to 350 grams for a measurement scale going from zero to 800 cN.

Conventionally, the tear tester is provided with a knife to make a beginning of a tear (not shown).

The microphone 4, here of the Shure SM58 brand, is positioned so as to be able to sense the above sounds in good conditions.

The tear tester is stripped of any device capable of generating interference noises during the recording of the sounds to be captured. Here its unblocking system in particular has been removed but this is not absolutely necessary.

The personal computer PC 5 is used here running the Windows® operating system. It is fitted with a sound card 6, here a Terratec model Sixpack 5.1+ card, and functional modules consisting essentially of software programs, particularly a recording program 7, here Nero Wave Editor of the Ahead Software brand, a standard signal analysis and processing software program 8 such as Spectrogram v8.8 marketed by Visualization Software, and a graphic software program 9 such as Photoshop v7.0 from Adobe.

The software 7 records the sound data originating from the sound card 6 in digital form in a first memory 10.

The software 8 processes the sound data of the first memory 10 and stores its analysis and processing data in a second memory 11 as will be specified hereinafter.

The PC 5 is connected to a man-machine interface comprising a keyboard 12 and a screen 13 capable of displaying the content of the memories 10 and 11 and incidentally a printer 14 of the universal printer type capable of printing the image present on the screen 13, but also of scanning the documents that it prints.

Figure 2:
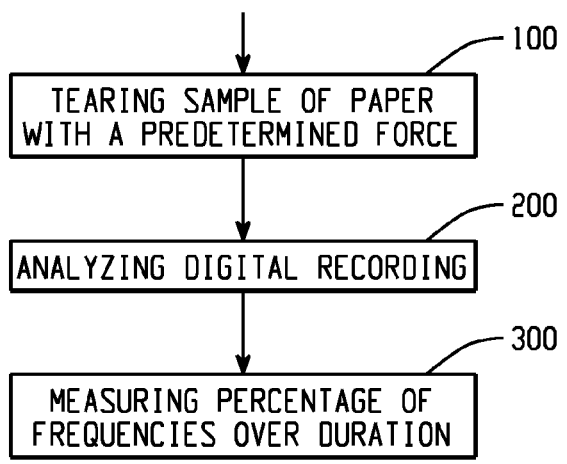
FIG. 2 represents a flow chart of the steps carried out to apply the method of measuring stiffness according to the invention.
Figure 6:
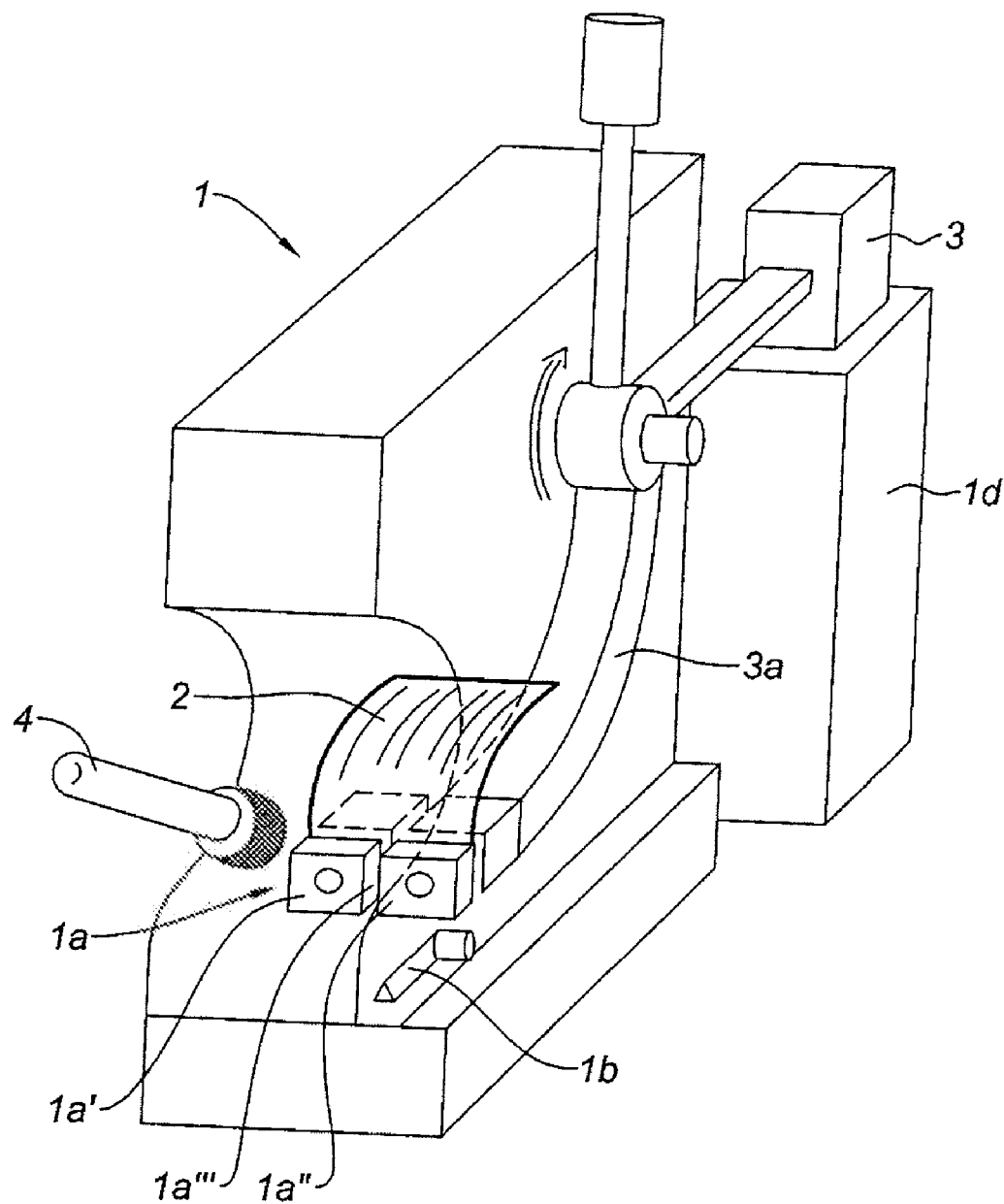
FIG. 6 shows an item of equipment for carrying out the tearing of a sample.

The method then comprises the following steps, with reference to FIG. 2:

During a first step 100, the paper is torn with the force predetermined by the weight P. For this, the paper 2 is placed in the tear tester 1 so that the direction of manufacture of the paper is in the direction of the tear. According to FIG. 6, the sample 2 is placed in the jaw 1a of the tear tester 1. This jaw is formed of two parts, one fixed 1a', the other movable 1a", a free space 1a''' is thus arranged between the two parts. The knife 1b is set in motion so as to pass into the free space 1a''' between the two jaws and make a beginning of a tear in the direction of the tear corresponding to approximately ⅙ of the length of the sample in the direction of manufacture. The pendulum 3 is in a stop position, a chock 1d immobilizing the weight of the pendulum. The chock 1d is removed from the pendulum while it is held in the start position by means of the lever arm 3a and sound recording is begun. The lever arm 3a of the pendulum 3 is swiftly released, which generates no interference noise. The pendulum 3 thus released pivots and sets the movable jaw 1a" in motion causing the sample to be completely torn.

During this step 100, the tearing emits sounds captured by the microphone 4 and recorded thanks to the sound card 6 and the software program 7 at a fairly high sampling frequency fe, here 44 100 Hertz with a resolution r of 16 bits. The software program 7 records sounds in digital form in the memory 10. The stored digital recording is of sufficient duration T to cover the whole duration of the emitted sound, thanks to the software program 7.

Figure 3:
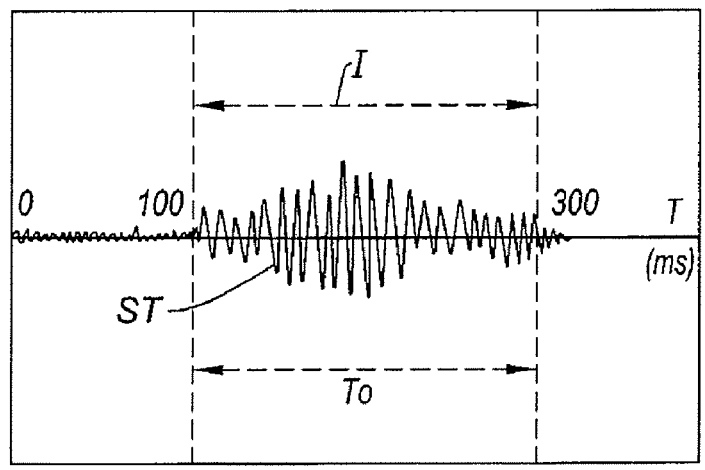
FIG. 3 represents a temporal recording of the sound obtained at the moment paper is torn.

During a subsequent second step 200, the digital recording of the memory 10 is analysed in the temporal and frequency domains in the following manner:

1) From the digital recording, thanks to the keyboard 12 and via the software program 7, a time interval I of predetermined duration, here 200 milliseconds lying between $T_0+100$ ms and $T_0+300$ ms, $T_0$ being the start of the sound spectrum, is selected. This gives a reduced digital recording or "temporal spectrum" ST as shown in FIG. 3. The time interval I of duration T is transmitted to the signal processing software program 8 in a format compatible with the two software programs 7 and 8, for example WAV (Windows Audio Video) which is a Windows sound file format.

Figure 4:
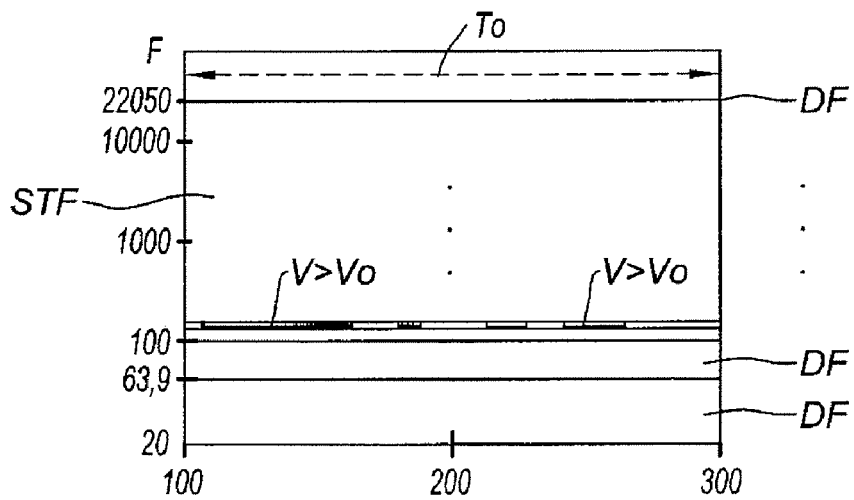
FIG. 4 represents a set of frequency spectra over the duration of the temporal recording, encoded according to a colour scale.

2) The software program 8 performs the fast Fourier transforms (FFT) on the spectrum ST, here 1024 dots in size, hence with a resolution DT, here of 0.195 millisecond, to obtain, with reference to FIG. 4, a set STF of "time-frequency" spectra in a logarithmic frequency and linear temporal scale, here comprising frequencies F from 20 to 22050 Hertz with a resolution DF equal to 43.1 Hertz. The amplitudes are encoded in colour according to a colour scale distributed so as to clearly differentiate the frequencies F of amplitudes V greater than a predetermined minimal amplitude Vo (V>Vo in the figure), and here corresponding to a sound volume of 20 dB. All these values are indicative and other settings could be defined to the extent that the coherence thereof is retained.

The amplitudes V must be sufficiently differentiated by the chosen colours to be able to be selected subsequently, for example coloured in dark colours. In FIG. 4, the colours are not shown, but the potential selection is made effective by the horizontal black hatching. A simple comparison carried out by software can make it possible to obtain this selection automatically.

Figure 5:
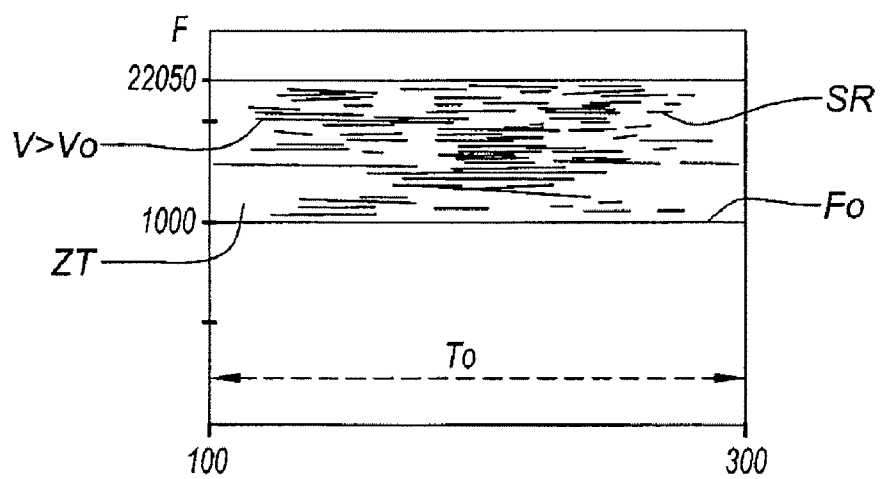
FIG. 5 represents the same set of spectra limited to the test zone.

The image of the set STF supplied by the software program 8 is stored in the memory 11 and may then be transmitted to the graphic software program 9 in the form of a new image shown in FIG. 5, of the same size as the definition of the PC screen, here 1024×1280 colour pixels. This transmission may for example be carried out by performing a print screen (the "print screen/sysRq" key of the keyboard 12) on the printer 14, the document thus printed then being scanned on the same printer 14 and the image obtained reduced by the software program 9 to a 1024×1280 image.

During a subsequent step 300, the percentage presence of frequencies Fc, called characteristic, over the duration To, is measured using the software program 9 which selects them by the means specified hereinabove. The printed document could be worked on manually using a hydrometer. These characteristic frequencies Fc are the frequencies F, present in the interval I of duration To, of amplitudes V greater than Vo and greater than a predetermined minimum frequency Fo. They are considered to be sufficiently characteristic of the sounds emitted during the tearing of the paper 2. More precisely:

1) The set STF of time-frequency spectra, with reference to FIG. 5 is limited to a zone ZT called the test zone comprising the frequencies F greater than the predetermined minimal frequency Fo. In the chosen example, Fo=1000 Hertz. Then, in this zone ZT, the relative surface area SR of the dark zones occupied by the frequencies F of amplitudes V greater than Vo are computed. For this, the zone ZT comprises a predetermined and still identical (1024×1280) total number of colour pixels NTP. In fact, the measurement of the relative surface area SR occupied by the frequencies Fc is then perfectly represented by the number of colour pixels N1 present on this surface SR. And the number N1 is itself perfectly representative of the percentage pc sought of presence of the frequencies F since:

$$pc=100\times N1/NTP \tag{20}$$

It is practical to use the number N1 directly since it can be evaluated simply by having the software program 9 produce a histogram of the dark coloured surfaces in the zone ZT.

Without being bound by the theory, the outcome of this method is that there is a close relationship between the cohesion, the inter-fibre links and the sound of the tear. The inter-fibre links may be caused by a more or less powerful refining of the fibre suspension or a partly damp pressing. The analysis of the tearing sound has a certain value for tissue papers that are called "stratified" (or layered) which may comprise an inner stratum (or layer) of stronger, longer and/or more refined fibres and an outer stratum (or layer) of softer, shorter and lightly bound fibres.

Since the measurements taken according to the aforementioned method depend only on physical and not subjective evaluations, they are faithful to within the physical measurement errors, which was indeed the objective sought.

The invention claimed is:

1. A method of measuring the stiffness of a paper or other cellulosic fibrous product comprising the steps of controllably tearing a sample of the paper, recording the sound generated during the tearing and analysing the recorded sound to determine the percentage of frequencies characteristic of the tearing present in the recording, this percentage being an indicator of the stiffness of the paper.

2. The method according to claim 1, in which the paper sample is torn in its direction of travel.

3. A method of measuring the stiffness of a sample of paper or other cellulosic fibrous product according to claim 1, characterized in that the method further comprises:
   a) tearing the sample with a predetermined force;
   b) digitizing the recording of the sound generated during the tearing at a predetermined sampling frequency (fe) and with a predetermined resolution (r) to obtain a digital recording (10, ST) of a predetermined duration (T);
   c) analyzing the digital recording in the temporal and frequency domains; and
   d) measuring and recording over said predetermined duration the percentage of the frequencies (Fc) characteristic of the tearing present in the digital recording.

4. The method according to claim 3, in which the paper sample is torn in its direction of travel.

5. The method according to claim 4, comprising the further step of outputting a signal representative of the stiffness of the paper sample in which use is made of at least one linear computational relation of the stiffness index (D) as a function of the percentage (pc) of the presence of the said frequencies (Fc) in the set (STF) of frequency spectra (STF) obtained over the duration (T) of the recording (ST).

6. The method according to any one of claims 3-5, in which, the analysis of the digital recording (ST) and the measurement of the percentage (pc) of the frequencies (Fc) characteristic of the tearing present in the digital recording comprises:
   a) performing a Fourier transform on the digital recording (ST) and providing a first output signal in the form of a display encoded in amplitudes according to a colour scale so as to distinguishably differentiate the frequencies (Fc) having amplitudes (V) at least equal to a predetermined minimal amplitude (Vo);
   b) providing a second output signal from the first output signal delimiting a test zone (ZT) comprising only the frequencies (Fc) greater than a predetermined minimal frequency (Fo) and which provides a visual indication of the relative surface area (N1) occupied by the frequencies (Fc) in this test zone having amplitudes (V) at least equal to the said minimal amplitude (Vo);
   c) computing a stiffness index (D) based on said relative surface area (N1); and
   d) providing a visual display of the stiffness index (D).

7. The method according to claim 6, in which the characteristic frequencies (Fc) are those obtained over the duration (T) of the digital recording (ST), greater than the minimal frequency (Fo), and having an amplitude (V) at least equal to the minimal amplitude (Vo) and the zone (ZT) comprises a predetermined total number (NTP) of colour pixels, and the stiffness index is based upon determining the number of pixels present on the surface area.

8. A device for measuring the stiffness of a sample of paper or other cellulosic fibrous product comprising:
   a) an apparatus arranged to tear a sample of paper in a manner that can be reproduced in identical conditions;
   b) a microphone for converting the sound signals obtained during the tearing into electrical signals;
   c) signal converting means connected to the microphone for providing a digital signal derived from the electrical signal output from said microphone;
   d) means for recording the digital signal;
   e) signal processing means for mathematically manipulating the recorded digital signal to determine the percentage of frequencies characteristic of the tearing present in the recording; and
   f) means for outputting a signal indicative of the stiffness of the paper based upon said percentage.

9. The device for measuring the stiffness of a sample of paper or other cellulosic fibrous product according to claim 8, wherein:
   a) the apparatus for tearing the paper sample tears with a predetermined force;
   b) the signal converting means digitizes the signal output from the microphone at a predetermined sampling frequency (fe) and with a predetermined resolution (r) to obtain a digital recording (ST) of a predetermined duration (T); and
   c) the signal processing means analyzes the digital recording in the temporal and frequency domains and outputs a signal representative of the percentage of the frequencies (Fc) characteristic of the tearing present in the recording.

10. The device for measuring the stiffness of a sample of paper or other cellulosic fibrous product according to claim 9, wherein the signal processing means outputs a signal representative of the stiffness of the paper sample based on at least one linear computational relation of the stiffness index (D) as a function of the percentage (pc) of the presence of said characteristic frequencies (Fc) in the set (STF) of frequency spectra (STF) obtained over the duration (T) of the digital recording (ST).

11. The device for measuring the stiffness of a sample of paper or other cellulosic fibrous product according to any one of claims 8-10, wherein the signal processing means for mathematically manipulating the recorded digital signal further comprises:
   a) means for computing a Fourier transform based on the digital recording (ST);
   b) means for providing an output signal therefrom in the form of:
      i) a display encoded in amplitudes according to a colour scale so as to distinguishably differentiate the frequencies (Fc) having amplitudes (V) at least equal to a predetermined minimal amplitude (Vo), the output signal being provided therefrom in the form of a display encoded in amplitudes delimiting a test zone (ZT) comprising only the frequencies (Fc) greater than a predetermined minimal frequency (Fo); and
      ii) a visual indication of the relative surface area (N1) occupied by the frequencies (Fc) in this test zone having amplitudes (V) at least equal to the said minimal amplitude (Vo); and c) means for providing a visual display of a signal indicative of a stiffness index (D) computed based on the said relative surface area (N1).

12. The device for measuring the stiffness of a sample of paper or other cellulosic fibrous product of claim 11, in which the characteristic frequencies (Fc) are those obtained over the duration (T) of the digital recording (ST), greater than the minimal frequency (Fo), and having an amplitude (V) at least equal to the minimal amplitude (Vo) and the zone (ZT) comprises a predetermined total number (NTP) of colour pixels, and the stiffness index is based upon determining the number of pixels (N1) present on the surface area (SR).

* * * * *